United States Patent [19]

Huber et al.

[11] Patent Number: 4,548,497
[45] Date of Patent: Oct. 22, 1985

[54] METHOD AND DEVICE FOR INTRODUCING A SAMPLE INTO A GRAPHITE TUBE

[75] Inventors: Bernhard Huber, Überlingen; Rolf G. A. Tamm, Salem; Toma Tomoff; Winfried Gönner, both of Überlingen, all of Fed. Rep. of Germany

[73] Assignee: Bodenseewerk Perkin-Elmer & Co., GmbH, Überlingen, Fed. Rep. of Germany

[21] Appl. No.: 422,635

[22] Filed: Sep. 24, 1982

[30] Foreign Application Priority Data

Nov. 25, 1981 [EP] European Pat. Off. ...... 81 109 879.7

[51] Int. Cl.⁴ ............................................. G01N 21/74
[52] U.S. Cl. .................................... 356/312; 356/244
[58] Field of Search .................... 356/312, 36, 244

[56] References Cited

U.S. PATENT DOCUMENTS 4,406,540 9/1983 Grossman et al. .................. 356/312
4,443,105 4/1984 Huber et al. ........................ 356/312

FOREIGN PATENT DOCUMENTS 2088582 6/1982 United Kingdom ................ 356/312

Primary Examiner—F. L. Evans
Attorney, Agent, or Firm—E. T. Grimes; J. D. Crane

[57] ABSTRACT

In a method for introducing a sample into a graphite tube in flameless atomic absorption spectroscopy a lamella- or crucible-like sample carrier is introduced into the graphite tube from the end face in axial direction. Drying and ashing of the sample is effected outside the graphite tube. The sample carrier may be heated indirectly by radiation or directly by electric current being passed therethrough.

5 Claims, 10 Drawing Figures

METHOD AND DEVICE FOR INTRODUCING A SAMPLE INTO A GRAPHITE TUBE

BACKGROUND OF THE INVENTION

The present invention generally relates to a method for flameless atomic absorption spectroscopy for introducing a sample into a graphite tube which is held at its ends by contact pieces and, in particular, relates to a method in which the sample is applied to a sample carrier which is moved into a first position outside the graphite tube where the sample is heated for ashing and thereafter the sample carrier is moved into a second position inside the graphite tube where the sample is atomized.

In a graphite tube atomizer a graphite tube is positioned between two annular contact pieces. Through the contact pieces, which are usually designed as cooling chambers flown through by a coolant, electric current can be passed through the graphite tube thereby heating it to high temperatures. In known graphite tubes, a lateral sample introducing aperture is provided on the sleeve surface, through which aperture a liquid sample can be introduced into the graphite tube. The graphite tube is then heated in several steps to dry the introduced sample, to ash it and finally to atomize it such that a "cloud of atoms" is formed within the graphite tube, in which "cloud of atoms" the different components of the sample are present in atomic state. The measuring light beam of an atomic absorption spectrophotometer passes longitudinally through the apertures of the annular contact pieces and through the longitudinal bore of the graphite tube. This measuring light beam is formed by a radiation generated, for example, by means of a hollow cathode lamp and which only contains the resonance lines of a sought element. Ideally, the measuring light beam is absorbed only by the atoms of the sought element in the cloud of atoms such that the attenuation of the measuring light beam is a measure of the quantity of the sought element in the sample.

Usually, a sample is present in liquid state as a solution. To prevent the measurement from being affected by the solvent and to ensure a rapid atomization of the sample for the measurement, the sample is dried at low temperature during which the solvent is vaporized. The drying is followed by "ashing" during which step the sample is thermally decomposed at a higher temperature. The ashing step may generate soot which is formed by non-vaporized components of the sample, which soot subsequently falsifies the measurement by non-specific absorption of the measuring light beam. These interfering components are usually removed before the measurement proper by means of an inert gas flow which passes through the graphite tube and prevents air from entering thereinto and thus prevents the graphite tube from burning.

In known graphite tubes of this type, the sample is injected such that it collects in about the middle of the graphite tube on the lower portion of the inner wall. The temperature of the graphite tube is usually varied for drying, ashing and atomizing according to a predetermined program.

Drying and ashing ordinarily take place inside the graphite tube, which is a straight tube, in the path of rays of the measuring light beam. Interfering components from the drying and ashing procedures, which components are not completely removed the graphite tube by the inert gas flow, may condense on the inner wall of the graphite tube and falsify the measurement.

In some cases, the atomizing temperature at which a sought element in the sample is atomized depends on the type of compound in which the element is present in the dried and ashed sample. If, then, the graphite tube is continuously heated after the ashing, it may happen that a sought element is first atomized out of one compound and then atomized out of another compound at a higher temperature. This leads to corresponding signals at the detector such that the unambiguity of the relation between peak height of the detector signal and quantity of the sought element is impaired.

For this reason, it is known to apply drops of the sample solution to a sample carrier, for example, a wire helix made of tungsten. The sample carrier with the sample solution is then moved in front of a lateral sample introduction aperture of the graphite tube. An inert gas flow is passed through the graphite tube from the ends and exits at the introduction aperture. If the graphite tube is heated, the exiting inert gas flow is also heated. The sample is thus dried by means of this hot inert gas flow and the vaporizing solvent does not enter the graphite tube. (Analytical Chemistry, Volume 51 (1979), 2375-2378).

When the sample carrier is moved closer to the graphite tube, the temperature of the sample carrier is further increased due to the heat transfer from the graphite tube, such that the dried sample is further heated and is thermally decomposed. This also occurs outside the graphite tube. Subsequently, the graphite tube is heated to the atomizing temperature. After this temperature has been reached, the sample carrier is quickly introduced into the graphite tube.

Interfering components from the drying and ashing procedure are thus prevented from condensing on the inner wall of the graphite tube. The dried and decomposed sample is heated to the atomization temperature in one step by inserting the sample carrier such that the atoms of the sought element get into the cloud of atoms simultaneously, independent of their chemical compound.

From West German OS No. 30 08 938 a graphite tube for flameless atomic absorption spectroscopy having a tubular graphite body is known which provides a lateral introduction aperture for introducing a sample and on which a tubular lateral projection is provided, which projection surrounds the introduction aperture. A drop of the sample solution is applied to a wire helix carrier. The carrier is moved in front of the introduction aperture of the graphite tube, such that with the graphite tube heated the sample is dried by means of the exiting flow of hot inert gas. Subsequently, the carrier is introduced into the tubular lateral projection of the graphite tube for thermal decomposition, and the graphite tube is then heated to the atomizing temperature.

From West German OS No. 30 09 784 a device for introducing a sample into a graphite tube in flameless atomic absorption spectroscopy having a sample carrier of electrically conducting material designed as to be introduced into the graphite tube is known in which device the sample carrier is provided with electric connections and controllably heatable outside the graphite tube by passing an electric current therethrough. The drying and ashing of the sample outside the graphite tube is effected by controllably heating the sample carrier. The sample carrier is moved into a lateral aperture of the graphite tube for atomization.

From West German OS No. 27 10 861 a device for introducing a sample into a graphite tube in flameless atomic absorption spectroscopy is known, in which a liquid sample is applied to the sample carrier and is dried by being heated before the sample carrier is introduced into the graphite tube. This device comprises a sample carrier in the form of a straight wire made of electrically conducting material, onto which spaced helical parts are threaded. The liquid sample is applied to these helical parts. The sample carrier is arranged to be introduced into the graphite tube, the straight wire being passed through aligned lateral apertures of the graphite tube, which wire thus transversely passes through the graphite tube. The wire is provided with electric connections and is heatable thereby. A pair of parallel legs are connected to the sample carrier and hold it. The legs are mounted on a carriage which is movable transversely to the longitudinal axis of the graphite tube. These legs extend transversely to the direction of movement of the carriage on both sides of the graphite tube and maintain the straight wire, which is transversely passed through the graphite tube between the legs. By stepwise advancing of the carriage, the wire is thus drawn stepwise through the graphite tube. In that way, consecutively the different helical parts having the samples supplied thereto get into graphite tube. In passing electric current through the straight wire, the sample liquids are dried and ashed outside the graphite tube. In this way, a plurality of samples may be analyzed quickly one after the other.

The known structure is designed for the quick analysis of a plurality of samples one after the other. However, it presents various problems.

The graphite tube atomizer must be provided with two aligned, transverse bores through which the wire is passed. That is, on opposite sides of the graphite tube, two relatively large apertures have to be provided. This accelerates the dissipation of the "cloud of atoms" formed inside the graphite tube.

A graphite tube is a component to be used up which is replaced after a certain number of analyses. As the wire is passed through the graphite tube with each replacement of the graphite tube, the wire has to be detached from the legs and the electric connections and, after the old graphite tube has been removed, has to be passed through the new graphite tube. This is a tedious and a time consuming procedure and which leads to quick wear of the device.

From the West German OS No. 2 219 190 a device for atomizing a sample for flameless atomic absorption spectroscopy is known, in which the sample is introduced into a small crucible of electrically conducting material. This crucible is held by two legs which are disposed close to but spaced from each other. It is heated to atomizing temperature by passing electric current through the crucible through the legs. The crucible is surrounded by a heated tubular retainer. In contrast to more conventional graphite tubes, the only function of the retainer is to keep together the "cloud of atoms" formed by the atomizing of the sample. The heating of the retainer is not to atomize the sample, but just to prevent a condensation of the sample atoms on the retainer. OS No. 2 219 190 also suggests moving the crucible out of the cavity defined by the retainer for carrying out a drying and ashing procedure.

From the West German OS No. 29 45 646 a method for applying solid or semi-solid samples to a graphite tube atomizer for flameless atomic absorption spectroscopy is known, in which method the sample is taken up by means of a tool the lateral dimensions of which permit an introduction of the tool into the dosing aperture which is usually provided on the sleeve surface of the graphite tube. The tool together with the sample is introduced into the graphite tube through this dosing aperture. The tool may comprise a kind of spoon which is formed to be rotated through 180° to spill a solid sample introduced within the graphite tube.

From the West German OS No. 2 023 336, there is furthermore known to tip aside a graphite tube atomizer having housing, contact pieces and graphite tube relative to the measuring light beam such that the graphite tube is accessible from one end through a contact piece. A solid sample may then be introduced from the end face of the graphite tube by means of a suitable tool.

SUMMARY OF THE INVENTION

Accordingly, one object of the present invention is to provide a device such that even rather large quantities of liquid samples as well as solid or powder-like samples may be supplied.

This object is achieved, at least in part, by a device wherein the sample is applied to a lamella- or crucible-like sample carrier and the sample carrier is moved into its second position below the measuring light beam in axial direction from the end face into the graphite tube.

Other objects and advantages will become apparent to one skilled in the art from the following detailed description and the accompanying drawing.

BRIEF DESCRIPTION OF THE DRAWING

The present invention is described in greater detail hereinbelow with reference to the accompanying drawing, which is not drawn to scale, and in which.

DETAILED DESCRIPTION OF THE INVENTION

Figure 1:
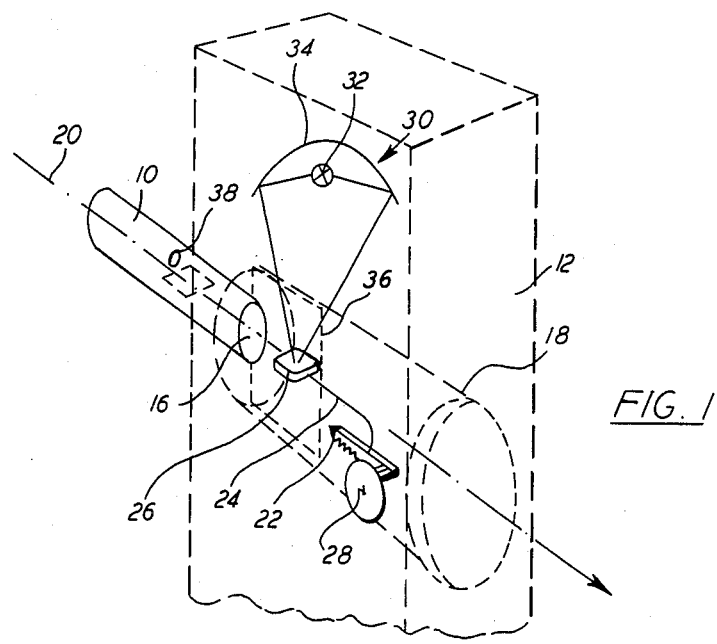
FIG. 1 is a schematic view of one embodiment of the present invention including a graphite tube atomizer and a device for introducing a sample thereinto.

A graphite tube, generally indicated at 10 in FIG. 1, is mounted at its ends between cooling chambers through which coolant flows, of which cooling chambers only cooling chamber 12 is shown in FIG. 1. The cooling chambers contact the graphite tube 10. The cooling chambers 12 are provided with an aperture 18 aligned with the longitudinal bore 16 of the graphite tube 10 to permit the passage therethrough of a measuring light beam 20. A carriage 22 having a holder 24 and a sample carrier 26 is disposed in the aperture 18 of one of the cooling chambers 12 below the path of rays of the measuring light beam 20, and is movably guided in the longitudinal direction of aperture 18 and graphite tube 10. The arrangement also includes a servomotor 28. A heating means 30, for example, in the form of a light source 32 and a reflector 34, for contactless heating of the sample carrier 26 is disposed in the cooling chamber. A dosage window 36 is provided in the cooling chamber 12 in the area of heating arrangement 30, through which dosing window the sample carrier 26 is accessible and through which vapor may exit during drying and ashing of the sample.

The carriage 22 with holder 24 and sample carrier 26 is arranged to be advanced, in a controlled manner by means of servomotor 28, in the direction towards the end face of the graphite tube and into the bore of graphite tube 10. In a first operative position of carriage 22, shown in FIG. 1, the sample carrier 26 is in the area of the heating arrangement 30 which is designed for contactless, or radiant, heating of the sample carrier 26. In a second operative position of carriage 22, shown in FIG. 1 in dashed lines, holder 24 with sample carrier 26 extends into the interior of the graphite tube 10.

This arrangement offers the advantage that conventional graphite tubes may be used. It is possible to alternately load the graphite tube 74 directly through a small introduction aperture 38 in conventional manner or by means of the sample carrier 26 described.

The holder 24 may be fabricated from a high melting metal, graphite, glassy carbon or the like. The sample is applied to the sample carrier 26. The sample carrier is moved into the first position outside the graphite tube 10, and there the sample is heated for ashing by means of the heating arrangement 30. Subsequently, the sample carrier is moved into a second position inside the graphite tube 10. There the sample is heated for atomization, in the present case, by heating the graphite tube 10. The lamella- or crucible-like sample carrier is moved in an axial direction from the end face into the graphite tube 10 into its second position below the measuring light beam 20.

A sample may be applied in solid state to the sample carrier.

The ashing of the sample in the first position is effected by means of a heating arrangement 30 which is separate from the graphite tube 10.

Figure 2:
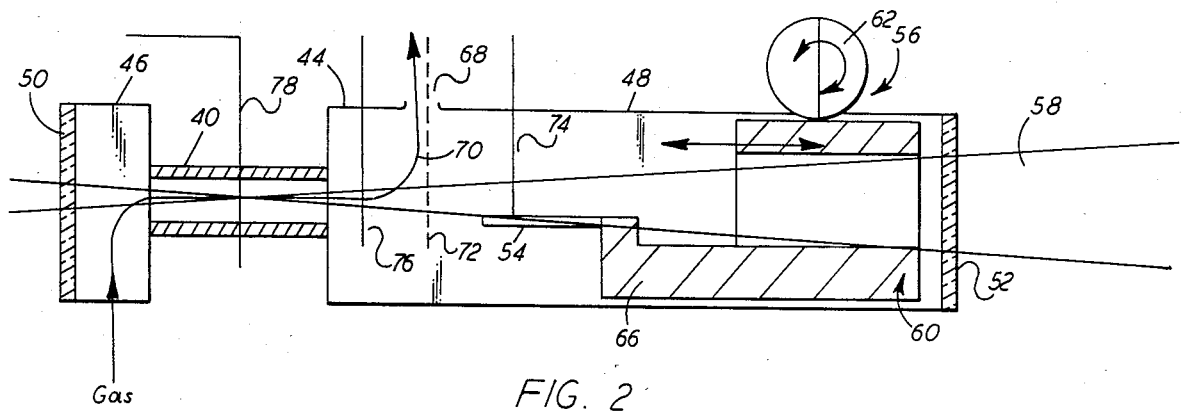
FIG. 2 is a schematic longitudinal cross-section of another embodiment of a graphite tube atomizer and a device for introducing a sample.

Another embodiment is shown in FIG. 2. Therein, the graphite tube 40 is clamped between two contact pieces 42 and 44 which are usually also designed as cooling chambers. The contact pieces provide apertures 46 and 48, respectively, aligned with the bore of the graphite tube 10, which apertures are closed by windows 50 and 52, respectively. The device comprises a sample carrier 54, to which the sample is applied and a device 56 for moving the sample carrier 54 into a first position outside the graphite tube 40, in which an ashing of the sample occurs, and into a second position inside the graphite tube 40, in which an atomization of the sample is effected. The sample carrier 54 is a lamella- or crucible-like shape as described in detail hereinbelow. The device 56 for moving the sample carrier is disposed in front of one end face of graphite tube 40 outside the path of the measuring light beam 58. The sample carrier 54 is movable from the end face in an axial direction below the measuring light beam 58 into the graphite tube 40 into its second position.

The device 56 for moving the sample carrier provides a carriage 60, rectilinearly guided in the longitudinal direction of the graphite tube 40, upon which carriage 60 the sample carrier 54 is affixed on the side facing the graphite tube and extending in the longitudinal direction of the graphite tube 40. A servomotor 62 is coupled to the carriage 60 by means of a rack and pinion, for example, via which servomotor the carriage 60 with the sample carrier 54 can be advanced in a controlled manner towards the end face of the graphite tube 40. The carriage 60 is preferably of annular shape having an aperture for the measuring light beam 58. Below the measuring light beam 58, it forms an axially projecting holder 66, to which the sample carrier is attached.

The cooling chamber 44, at its end on the side facing the graphite tube, has a lateral dosing window 68 for introducing the sample. In the embodiment of FIG. 2, the carriage 60 is movable by means of the servomotor 62 into a sample supplying position, into a retracted position, into an ashing position and into an atomizing position. In the sample supplying position, the sample carrier 54 is disposed below the dosing window. In the retracted position, the sample carrier 54 is disposed on the side of the dosing window 68 remote from the graphite tube 40. In the ashing position, the sample carrier 54 is disposed between dosing window 68 and the end face of the graphite tube 40. In the atomizing position, the sample carrier 54 extends into the graphite tube. In FIG. 2, the sample supplying position is shown by line 72, the retracted position is shown by line 74, the ashing position is shown by line 76, and the atomizing position is shown by line 78. In FIG. 2, the sample carrier 54 is in its retracted position.

In the embodiment of FIG. 2, the sample carrier 54 is at first moved into its sample supplying position 72. The sample is supplied through dosing window 68. Subsequently, sample carrier 54 is advanced into its ashing position 76. The graphite tube 40 is heated. The inert gas flowing through the graphite tube 60 and heated accordingly flows over the sample and the sample carrier. Thereby, a heating of the sample up to the ashing temperature is effected such that a thermal decomposition takes place. The smoke which is eventually formed is carried away through the dosing window 68 by the inert gas flow and does not enter the graphite tube 40. Likewise, the evaporating solvent is carried away by the gas flow.

Then the sample carrier 54 is moved back to its retracted position. Now the graphite tube may be heated to the atomizing temperature. When this atomizing temperature is reached, the sample carrier 54 is quickly advanced to the atomizing position 78. Then follows a quick heating and atomization of the sample such that a sought element, even if originating from different compounds, is liberated at about the same time and contributes to the measuring peak at the same time.

Figure 5:
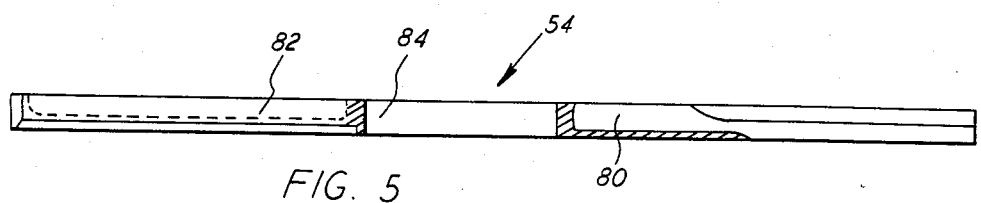
FIG. 5 is an associated longitudinal sectional view.
Figure 4:
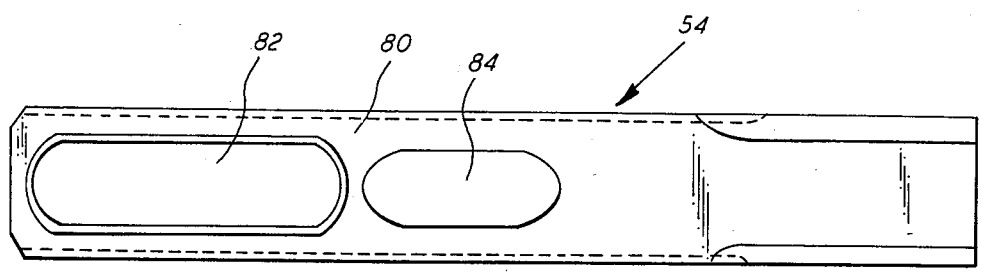
FIG. 4 is a plan view of a sample carrier preferably used in the embodiment of FIG. 2.

A preferred embodiment of the sample carrier 54 is shown in FIGS. 4 and 5. The sample carrier 54 is formed by an elongated flat part 80 of substantially rectangular shape. The part 80 provides a shallow recess 82 at its left end in FIGS. 4 and 5. The part 80, in its middle area longitudinally spaced from recess 82, provides an aperture 84. The aperture 84 reduces the heat transfer to the right end of part 80 which is clamped into holder 66. Thereby, the heating of the sample to ashing temperature is facilitated.

The use of a "passively heated" sample carrier 54 according to FIGS. 4 and 5 is advantageous in that the sample carrier may be easily mounted and has a simple shape. Also relatively large quantities of sample may be introduced.

As the heat for heating the sample during the ashing procedure in the ashing position 76 has to be transferred from the graphite tube 40 to the sample and the sample carrier 54, relatively long analyzing periods result. For the atomization, too, heat has to be transferred from the graphite tube 40 to the sample in the atomizing position 78. The rate of heating is not variable. With high melting elements, this may lead to problems.

For this reason, an "active" sample carrier is provided in the embodiment according to FIG. 3 and FIGS. 6 to 8, which sample carrier is heatable by passing electric current therethrough.

Figure 3:
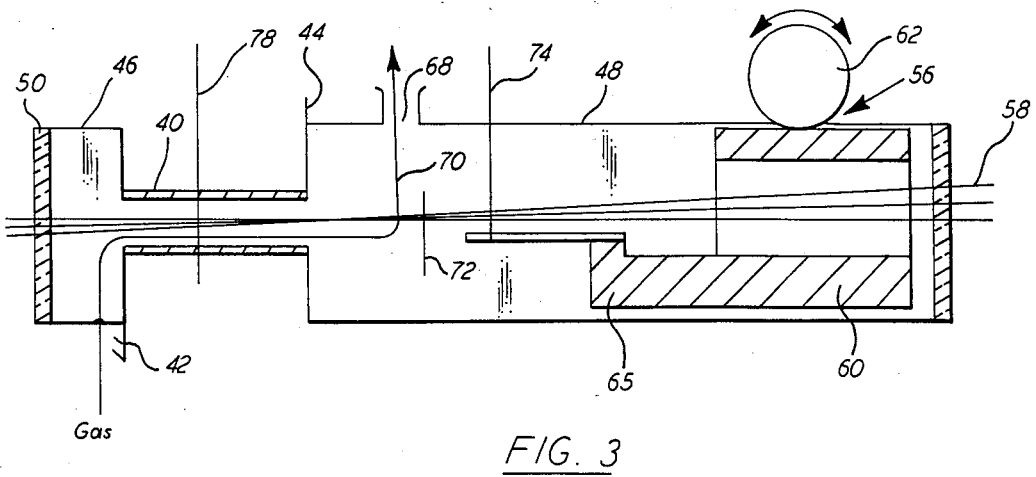
FIG. 3 is a view similar to FIG. 2 showing a third embodiment of the device.

The basic construction in FIG. 3 is the same as that in FIG. 2, and corresponding elements are designated by the same numerals.

In the embodiment according to FIG. 3, the carriage 60 is only movable between three positions by servomotor 60, namely the sample supplying position, the retracted position and the atomizing position. In the sample supplying position, the sample carrier 54A is again disposed below the dosing window 68. In the retracted position, the sample carrier 54A is disposed on the side of the dosing window 68 remote from the graphite tube 40. In the atomizing position, the sample carrier 54A extends into the graphite tube 40.

Figure 6:
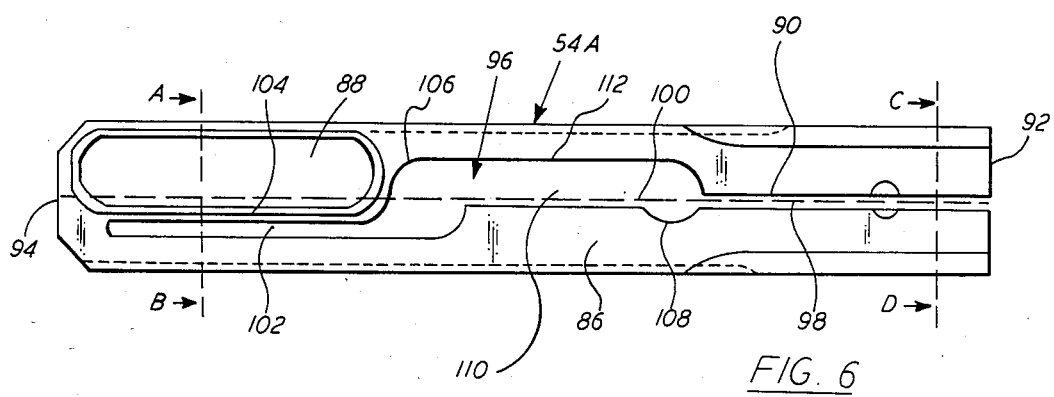
FIG. 6 is a plan view of a sample carrier preferably used in the embodiment of FIG. 3.
Figure 7:
FIG. 7 is a sectional view taken along line A-B of FIG. 6.
Figure 8:
FIG. 8 is a sectional view taken along line C-D of FIG. 6.

The sample carrier 54A is shown in detail in FIGS. 6 to 8.

The sample carrier 54A is also formed by an elongated flat part 86 of substantially rectangular shape providing a shallow recess 88 at one end. The recess 88 is laterally displaced in part 86. A longitudinal slot 90 is formed in part 86, which slot extends from the first end 92 remote from the recess 88 over nearly the whole length of part 86, laterally passing the recess 88, to shortly in front of the second end 94. Here also, part 86 provides an aperture 96 in its middle area longitudinally spaced from recess 88. The slot 90 provides a first straight portion 98 extending from the first end substantially along the center line 100 of part 86. The elongated aperture 96 disposed in longitudinal direction of part 86 joins the first straight portion 98. Another straight portion 102 departs from the aperture 96 which portion is laterally displaced with respect to the center line 100 and extends along a lateral edge 104 of the elongated recess 88 unsymmetrically disposed with respect to the center line 100. The aperture 96 contains two spaced bores 106 and 108 symmetric with respect to the center line 100 which are connected by an enlarged third slot portion 110 which is displaced to one side (to the top in FIG. 6) with respect to the center line 100, the one edge 112 of which slot portion extends tangentially to the cross-sections of both bores 106 and 108. The first portion 98 of the slot 90 ends in the bore 108. The second portion 102 of the slot is displaced to the other side (to the bottom in FIG. 6) and extends tangentially to the cross-section of the other bore 106.

Thus, the sample carrier is substantially U-shaped. Through the legs, an electric current can be passed through the sample carrier, which is heavily heated especially in the area of the recess 88. It has been found that the form described is particularly advantageous with respect to the local generation of Joule heat and with respect to the heat transfer to holder 66.

In the embodiment according to FIG. 3 and FIGS. 6 to 8, the sample carrier 54A is at first moved into the sample supplying position 72 below the dosing window 68. In this position, the sample is supplied to the sample carrier 54A. Subsequently, the sample carrier 54A is heated by electric current being passed through in the same position such that (if required) the sample is dried and ashed. Solvent vapors and soot are carried away through the dosing window 68 by means of the inert gas flow 70. The distance between sample carrier 54A and graphite tube 40 may be chosen to be relatively large, as the sample carrier needs not to be heated by the graphite tube 40 for drying and ashing. Accordingly, the graphite tube 40 is less affected by solvent vapors and smoke.

Subsequently, the sample carrier 54A is moved into the retracted position 74 by the carriage 60 and the servomotor 62. In this position, the sample carrier 54A is at such a distance from the graphite tube 40 that, during the heating of the graphite tube 40 to atomizing temperature, it is not heated indirectly to an undesired high temperature. Thus, interesting sample components cannot vaporize and prematurely be carried away by the inert gas flow 70. When the graphite tube 40 is heated to atomizing temperature, the sample carrier 54A is advanced into the atomizing position 78. The sample carrier 54A can also be heated by directly heating the sample carrier 54A, namely by passing electric current therethrough. Thereby, the rate of heating may be influenced, which results in higher sensitivity with high melting elements.

The arrangement described furthermore permits reduction of the analysis time. It is possible to adapt the heating to optimum analyzing conditions.

This arrangement, however, requires a larger expenditure of apparatus in the heating system and a larger expenditure of service, as two power supply units have to be provided and adjusted, one for the sample carrier 54A and one for the graphite tube 40.

Figure 10:
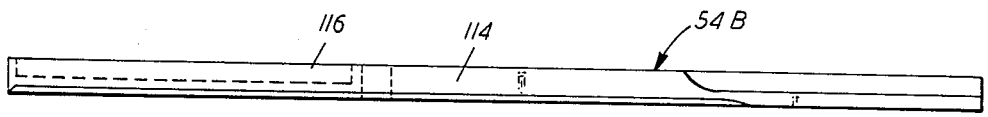
FIG. 10 shows an associated side elevation.
Figure 9:
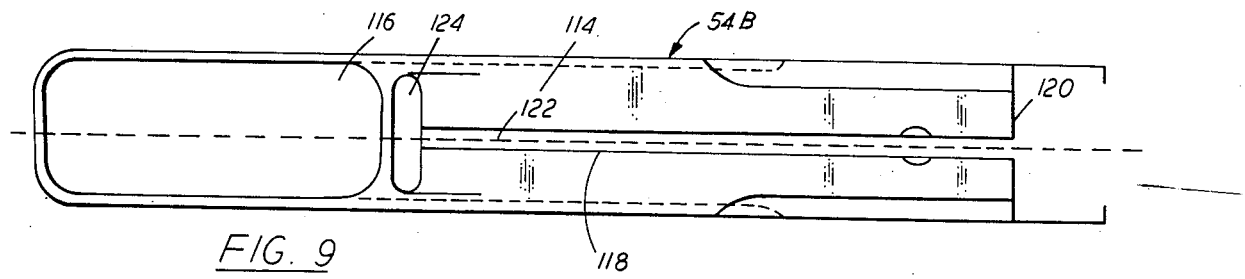
FIG. 9 is a plan view of another embodiment of a sample carrier.

FIGS. 9 and 10 show yet another embodiment of a sample carrier 54B, which embodiment may also be employed with an apparatus according to FIG. 3. There, too, the sample carrier 54B consists of a flat part 114 of substantially rectangular shape, which part provides a shallow recess 116 at one end. The recess 116 here substantially extends over the entire width of part 114 such that a relatively large quantity of sample may be applied. Here, too, a longitudinal slot 118 is formed within part 114, which slot extends from the first end 120 remote from the recess 116 of part 114. The longitudinal slot 118 extends from the end 120 along the center line 122 of part 114 to shortly in front of the recess 116. There, the longitudinal slot 118 communicates with a transverse slot 124 extending nearly over the entire width of part 114 and closed at the ends.

Although the present invention has been described herein with respect to specific embodiment other arrangements and modifications are also possible without departing from the scope and spirit of the present invention. Thus, the present invention is deemed limited only by the appended claims and the reasonable interpretation thereof.

What is claimed is:

1. Device for introducing a sample in a graphite tube comprising:
   a lamella- or crucible-like sample carrier to which said sample is applied, said sample carrier being formed of an elongated flat part of substantially rectangular shape, which flat part provides a shallow recess on one end, said recess is laterally displaced on said part, said part including a longitudinal slot extending from the first end remote from said recess over nearly the entire length of said part laterally past said recess to shortly in front of the second end;

means for moving the sample carrier into a first position outside said graphite tube whereat ashing of said sample is accomplished, said means being disposed of in front of an end face of said tube and outside of the path of rays of a measuring light beam;

means for moving said sample carrier into a second position inside said graphite tube whereat atomization of said sample is effected, said means maintaining said sample carrier below said measuring light beam.

2. Device as claimed in claim 1 wherein said part provides an aperture in its middle area longitudinally spaced from said recess.

3. Device as claimed in claim 2 wherein:

said slot provides a first straight portion extending from said first end substantially along the center line of said part;

an elongated aperture joins the first straight portion; and a second straight portion departs from said aperture which second portion is laterally displaced with respect to said center line and extends along a lateral edge of said shallow recess disposed unsymmetrically with respect to said center line.

4. Device as claimed in claim 3 wherein:

said aperture includes two spaced bores symmetric with respect to said center line which bores are interconnected by an enlarged third slot portion displaced to one side with respect to said center line, the one edge of which slot portion extends tangentially with respect to the cross-sections of both bores, the first portion of the slot ending in one bore; and the second portion of said slot being displaced to the other side and extends tangentially with respect to the cross-section of the other bore.

5. A device for introducing a sample into a graphite tube comprising:

a lamella- or crucible-like sample carrier to which said sample is applied, said sample carrier being formed by an elongated flat part of substantially rectangular shape, which flat part provides a shallow recess on one end thereof, said part includes a longitudinal slot formed along its center line which longitudinal slot extends from the end remote from said recess to shortly in front of said recess and communicates with a transverse slot extending over nearly the entire width of said part and closed at its ends;

means for moving said sample carrier into a first position outside said graphite tube whereat ashing of said sample is accomplished, said means being disposed in front of an end face of said tube and outside of the path of rays of a measuring light beam; and means for moving said sample carrier into a second position inside said graphite tube whereat atomization of said sample is effected, said means maintaining said sample carrier below said measuring light beam.

* * * * *